US005746714A

United States Patent [19]
Salo et al.

[11] Patent Number: 5,746,714
[45] Date of Patent: May 5, 1998

[54] AIR POWERED NEEDLELESS HYPODERMIC INJECTOR

[75] Inventors: Timothy J. Salo, Seattle, Wash.; Sergio Landau, Laguna Niguel, Calif.; Glenn D. Austin; T. Patrick Lennon, both of Seattle, Wash.

[73] Assignees: P.A.T.H., Seattle, Wash.; Vitajet Corporation, Laguna Hills, Calif.

[21] Appl. No.: 483,192

[22] Filed: Jun. 7, 1995

Related U.S. Application Data

[63] Continuation-in-part of Ser. No. 215,037, Mar. 18, 1994, abandoned, which is a continuation-in-part of Ser. No. 43,476, Apr. 5, 1993, abandoned.

[51] Int. Cl.⁶ ..................................................... A61M 5/30
[52] U.S. Cl. .............................. 604/68; 604/72; 604/143; 604/147
[58] Field of Search .............................. 604/68–72, 140, 604/141, 143, 147

[56] References Cited

U.S. PATENT DOCUMENTS

| | | |
|---|---|---|
| 2,821,193 | 1/1958 | Ziherl et al. . |
| 3,292,622 | 12/1966 | Banker . |
| 3,330,276 | 7/1967 | Gordon . |
| 3,330,277 | 7/1967 | Gabriels . |
| 3,462,867 | 8/1969 | Zimmet et al. . |
| 3,518,990 | 7/1970 | Banker . |
| 3,526,225 | 9/1970 | Isobe . |
| 3,763,859 | 10/1973 | Yanof et al. . |
| 3,853,125 | 12/1974 | Clark et al. . |
| 3,859,996 | 1/1975 | Mizzy et al. . |
| 3,908,651 | 9/1975 | Fudge . |
| 4,103,684 | 8/1978 | Ismach . |
| 4,124,024 | 11/1978 | Schwebel et al. . |
| 4,266,541 | 5/1981 | Landau . |
| 4,342,310 | 8/1982 | Lindmayer et al. . |
| 4,403,986 | 9/1983 | Dettbarn et al. ............... 604/70 |
| 4,411,650 | 10/1983 | Dettbarn et al. ............... 604/72 |
| 4,421,508 | 12/1983 | Cohen ............................. 604/70 |
| 4,560,377 | 12/1985 | Geat et al. ...................... 604/68 |
| 4,592,742 | 6/1986 | Landau .......................... 604/71 |
| 4,596,556 | 6/1986 | Morrow et al. ................ 604/70 |
| 4,623,332 | 11/1986 | Lindmayer et al. ........... 604/68 |
| 4,626,242 | 12/1986 | Fejes et al. .................... 604/68 |
| 5,049,125 | 9/1991 | Accaries et al. ............... 604/70 |
| 5,064,413 | 11/1991 | McKinnon et al. ........... 604/70 |
| 5,256,142 | 10/1993 | Colavecchio .................. 604/68 |

FOREIGN PATENT DOCUMENTS

| | | |
|---|---|---|
| 0 119 286 A1 | 9/1984 | European Pat. Off. ......... A61M 5/30 |
| 0 133 471 A1 | 2/1985 | European Pat. Off. ......... A61M 5/30 |
| 1499582 | 10/1967 | France . |
| 2 630 010 | 10/1989 | France ............................. A61M 5/30 |
| 33 28 173 A1 | 2/1985 | Germany . |

*Primary Examiner*—Michael Powell Buiz
*Assistant Examiner*—A. T. Nguyen
*Attorney, Agent, or Firm*—Seed and Berry LLP

[57] ABSTRACT

A needleless, low pressure, air powered medicine injector with a quick disconnect medicine delivery assembly removably connected to the injector housing. Low pressure air drives a biased piston through a discharge stroke, beginning from the retracted position into the medicine chamber, thereby forcing medicine through a one-piece nozzle. A removable chamber filling mechanism connected to the housing is coupled to the medicine chamber through fill ports, such that the medicine chamber is filled utilizing a positive pressure medicine distributor. A movable spacer collar positioned in front of the nozzle provides an air gap between a patient's skin and the one-piece nozzle. A safety interlock coupled to an activating mechanism and the chamber filling mechanism prevents unwanted discharge of the injection.

13 Claims, 6 Drawing Sheets

AIR POWERED NEEDLELESS HYPODERMIC INJECTOR

RELATED APPLICATION

This application is a continuation-in-part of U.S. patent application Ser. No. 08/215,037, filed Mar. 18, 1994, now abandoned, which was a continuation-in-part of U.S. Pat. No. 08/043,476, filed Apr. 5, 1993, now abandoned.

DESCRIPTION

FEDERALLY-SPONSORED RESEARCH AND DEVELOPMENT

This invention was made in part with Government support under Cooperative Agreement Number DPE-5968-A-00-0025-00 awarded by the Agency for International Development. The U.S. Government has certain rights in this invention.

TECHNICAL FIELD

The present invention relates to a liquid medicament injector and, more particularly, to a needleless liquid medicament hypodermic injector.

BACKGROUND OF THE INVENTION

For years health workers have administered medicine to patients using syringes and needles. However, use of syringes and needles put the health workers and patients at risk of infection through inadvertent needle-sticks or other equipment misuse. In addition, syringes and needles are difficult to disinfect or sterilize, and the use of improperly sterilized syringes and needles greatly increases the risk of blood-borne disease transmission among injection recipients. Reuse of dull needles can also cause extreme discomfort to the injected patient.

Disposable syringes and needles have been used to alleviate the risk of disease transmission. However, these disposable units create hazardous medical waste and waste disposal problems. In some areas of the world, disposable syringes and needles often do not reach the users in adequate quantities. As a result, these disposable units are used more than once. A further drawback to disposable syringes and needles are the high costs when the units are provided for worldwide use.

Several types of needleless injectors have been developed to avoid some of the drawbacks of syringes and needles. Mass-campaign jet injectors, such as the PEDOJET, have been used to provide fast and efficient needleless injections. However, these units are very difficult to clean or sterilize upon contamination. In addition, the mass-campaign injectors utilize a complex fluid path with dead space therein, such that a substantial amount of residual medicine is retained in the fluid path. When changing from one injectant to another, the residual fluid must be cleared to prevent unacceptable mixing of medicines. This clearing process wastes a relatively large amount of medicine before the injector is ready to inject another patient. It is to be understood, for purposes of simplicity, that "medicine" as referred to hereinafter is synonymous with all liquid medicaments and vaccines.

Low-workload jet injectors, such as the VITAJET or the SICIM HYPODERMIC INJECTOR JET 2000 have also been used to provide needleless injections. These low-workload jet injectors are typically effective for individual use. However, they are not sufficiently durable to accommodate an increased workload, e.g., several thousand injections, without requiring repair or maintenance. These low-workload injectors also utilize a complex fluid path that retains residual medicine. Accordingly, the units are difficult to sterilize, and medicine is wasted through purging when changing between medicines to be administered.

Many of the existing needleless injectors utilize two-piece nozzles that have gaps or seams in which blood or other material may accumulate. The injectors are also designed such that the nozzle directly contacts the patient's skin during an injection. The accumulation of foreign material in the nozzle and the skin contact increases the risk of contaminating the nozzle and/or a patient if blood is drawn by the injection. Thus, the sterilization difficulty and the possibility of nozzle contamination create an inherent risk to health workers and patients when injections are administered with existing jet injectors.

Operation of the prior art needleless injectors requires heavy springs, or high pressure, compressed gas to drive a piston that forces the medicine out of the nozzle. The heavy springs must be compressed or cocked prior to every injection. Unless the springs are cocked by high impact, high stress, or high pressure systems, such as a hydraulic system used by the PEDOJET, the spring powered units require slow mechanical cranking, systems that greatly limit the speed at which multiple injections may be administered. In addition, the spring driven units involve violent interactions between the springs, the piston, and the medicine chamber components. Improper use of the injector, such as firing the device without medicine or liquid in the chamber, can result in severe damage to the unit, thereby requiring costly repairs.

The injection devices that use high pressure gas, such as $CO_2$, are fairly expensive to operate because of the need for self-contained high pressure gas. The $CO_2$ units experience similar drawbacks and problems with sterilization, wasting medicine, and lack of durability during operation.

SUMMARY OF THE INVENTION

Accordingly, it is an object of the present invention to provide a low cost, durable, low-to-medium workload, air powered needleless injector that greatly alleviates the risk of disease transmission through injections, and that has few repair or maintenance requirements.

It is a further object of the present invention to provide a needleless injector that is not powered by heavy springs or high pressure gas.

It is a further object of the present invention to provide a needleless injector having a non-complicated, removable fluid path with essentially no dead space. Accordingly, the medicine can be changed without purging or wasting medicine while avoiding any mixing of the old with the new medicine thus allowing for easy and efficient changes in medicine.

It is another object of the present invention to provide a needleless injector that greatly reduces the risk of nozzle contamination by blood accumulations.

It is a further object of the present invention to provide a needleless injector that does not rely on negative pressure or suction to fill the medicine chamber prior to the injection.

It is yet a further object of the present invention to provide a needleless injector that greatly reduces medical waste and disposal thereof, while delivering accurate doses of medicine with little discomfort to the recipient.

These and other objects of the invention are obtained by using a needleless injector powered by low pressure ambient air, wherein the injector assembly includes a main housing connected to a low pressure air source, an air powered driving piston in the housing, and a removable medicine delivery unit engaging the air piston. The delivery unit mounts in the housing's front end, and has a medicine chamber with a fill port, a one-piece nozzle connected to the chamber, and a discharge piston slidably mounted in the chamber. The delivery unit of the invention does not use the check valves and washers of prior art units. The resulting delivery unit has almost no dead space and requires no disassembly for cleaning and/or sterilization. The air piston drives the discharge piston through its discharge stroke as low pressure air causes the air piston to slide. A safety interlock coupled to an injector activating mechanism is provided to protect against inadvertent discharge of the injector and resulting injury to health workers or patients.

The medicine delivery assembly of the subject invention further includes a medicine vial holder removably connected to the main housing and coupled to a medicine chamber filling mechanism. The filling mechanism utilizes positive pressure to drive medicine into the delivery unit's medicine chamber. A moveable spacer collar connects to the main housing and can be moved into a position in front of the nozzle, such that an air gap is created between the nozzle and the spacer. Upon activation, the injector fires a focused stream of medicine at high pressure through the nozzle, across the air gap, through an opening in the spacer, and into the awaiting patient.

BRIEF DESCRIPTION OF THE DRAWINGS

The above and other objects of the present invention will be more clearly understood from the following detailed description of the preferred embodiment taken in conjunction with the attached drawings.

DETAILED DESCRIPTION OF THE INVENTION

Figure 1:
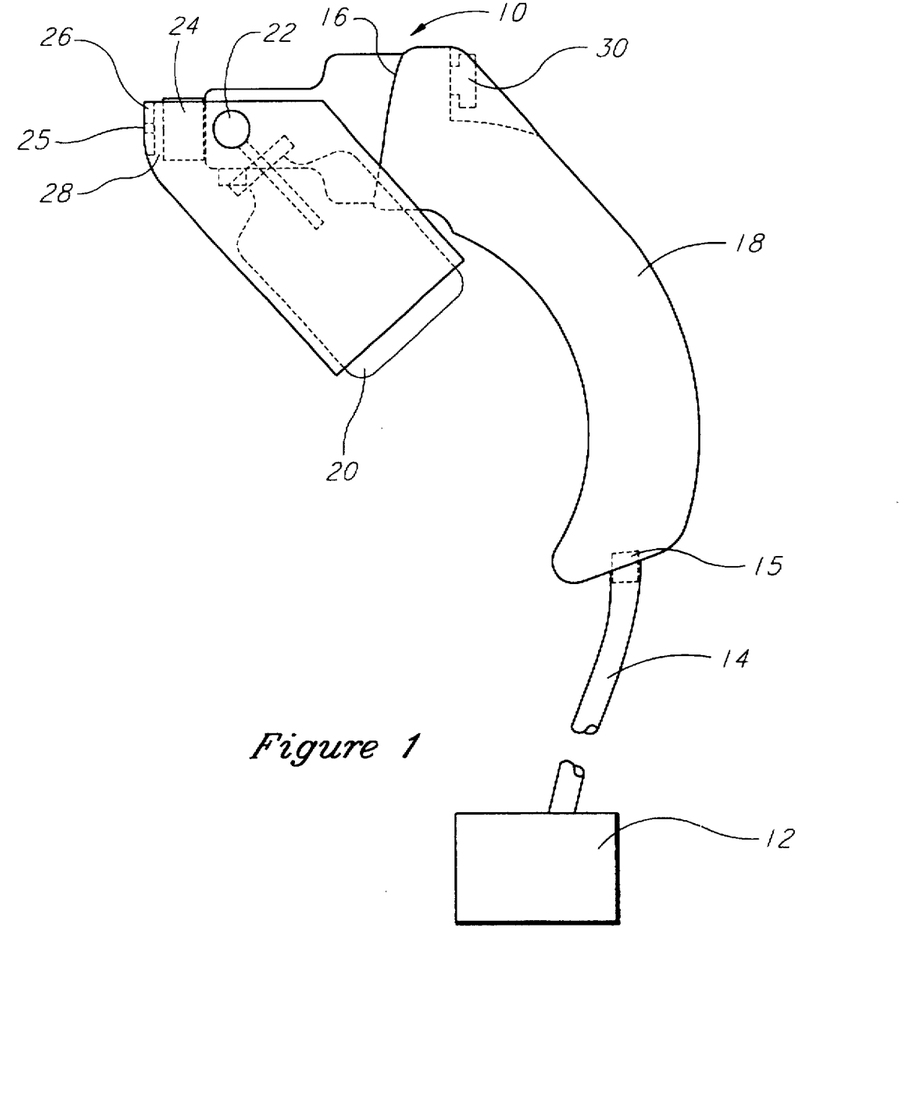
FIG. 1 is a schematic representation of the needleless injector with a medicine chamber filling mechanism attached thereto.

In accordance with the preferred embodiment of the present invention, as shown in FIG. 1, the housing 16 of the needleless hypodermic injector assembly 10 is connected to a low pressure air pump 12 or any other pressurized air source by an air hose 14. The hose 14 may either be permanently attached to the housing 16, or attached to the housing 10 by a quick disconnect mechanism 15 within the housing's handle 18, thereby facilitating efficient attachment to the pump 12. The assembly 10 utilizes low pressure air from the pump 12 to effectively administer a needleless injection to a patient.

Medicine loads into the assembly 10 from a medicine vial 20 and a medicine distributor 22 connected to the housing 16, and is ejected through a nozzle 24. A spacer 26 is movably carried by the filling mechanism 100, such that an air gap 28 is formed when the spacer 26 is positioned adjacent to the nozzle 24. When an operator depresses an injector activating mechanism, such as a "fire" button 30, the low pressure air supply causes a very narrow, highly focused stream of medicine to be ejected under high pressure through the nozzle 24, across the air gap 28, through an opening 25 in the spacer 26, and into an awaiting patient.

Referring to FIGS. 2, 3A, 3B, and 4, the needleless hypodermic injector assembly 10 incorporates several components. As indicated above, the hose 14 releasably connects to the housing's handle 18. A second length of pressurized air hose 36 extends through the handle 18 and connects, with a conventional hose connecting mechanism, to an air passage 38 within the main housing 16. The passage 38 communicates with a valve insert 42 that contains an activation valve 44 and the fire button 30. A spring 46 engages the fire button 30, thereby biasing the button 30 to a retracted ready position 48.

Upon depressing the button 30, the activation valve 44 slides within the valve insert 42 to an open position, unblocks the air passage 38, and exposes an air port 50. The port 50 is connected to an air chamber 54 formed by a cylinder 52 within the housing 16. An air piston 56, serving as a driving piston, is slidably mounted within the pressurized air chamber 54, such that when the activation valve 44 is in the open position, the low pressure air rushes through the passage 38 and the port 50, and the air piston 56 is instantaneously driven forward within the air chamber 54. A sufficient seal is maintained between the air piston 56 and the surrounding cylinder 52 by an O-ring 58. Similarly, a sufficient seal is maintained between the valve 44 and the insert 42 by an O-ring 45.

A medicine delivery unit 62 detachably mounts in the main housing 16 and comprises a cylindrical wall 65 having a circumferential shoulder on the outer forward end with an O-ring 114 therein, said wall defining a medicine chamber 64 with a medicine fill port 67 and a discharge piston 60. The nozzle 24 is threaded into the outside of the forward end of the wall 65 and is in sealing engagement with O-ring 114. Alternatively, the nozzle 24 may simply be welded to wall 65 or insert molded in chamber 64. The piston 60 has a piston head 78 and a rear rod extension 61 on which a biasing mechanism, such as a spring 66 is sleeved. The forward end of the spring engages a fitting 68 that, in turn, is seated at the rear of the medicine chamber 64. At its rear end, the rod 61 has an enlarged head 70 retaining the spring 66 and detachably engaging a recess 71 in the air piston 56. The piston 60 has a discharge stroke within the medicine chamber 64 from a retracted start position 72, to a finished, discharge position 73 adjacent to the nozzle 24. The biasing spring 66 automatically returns the piston 60 to the retracted position 72 after medicine has been delivered.

When the fire button 30 is depressed, the activation valve 44 snaps to the open position, and low pressure air rushes into the air chamber 54. As a result, the air piston 56 is instantaneously driven forward, thereby driving the discharge piston 60 through its discharge stroke within the medicine chamber 64. Any medicine contained within the medicine chamber 64 is forced through an ejection orifice 74 in the nozzle 24. The piston head 78 is sealed by its threaded cap bearing against O-ring 76. A close fit tolerance between the piston head and the wall 65 ensures all of the medicine within the medicine chamber 64 will be discharged during the discharge stroke. This, together with the almost total absence of dead space ensures that virtually no residual medicine remains in the medicine chamber 64 after administering an injection whereas in prior art devices the check valves and washers can create enough dead space to add up to as much as one-third of a 0.5 cc. dose of medicine.

Since the discharge piston 60 detachably engages the air piston 56, the entire delivery unit 62 may be detached as a unit from the main housing 16. A quick disconnect mechanism 80, installed in the housing's front end portion 81, secures the delivery unit 62 within the housing 16. The disconnect mechanism 80 slidably mounts in the front end portion 81, and a spring 82 biases the disconnect mechanism 80 in a securing position. The delivery unit has a beveled nose 83 at the rear, so that as the delivery unit 62 is installed into the front of the main housing 16, the beveled nose 83 engages and pushes the disconnect mechanism 80 upward, thereby compressing the spring 82. When a securing channel 86 formed in the delivery unit 62 aligns with the disconnect mechanism 80, the spring 82 drives the mechanism 80 down into the channel 86. Thus, the interface between the disconnect mechanism 80 and securing channel 86 effectively holds the delivery unit 62 in place. Proper radial orientation of the medicine chamber 64 and associated medicine fill port 67 is achieved by an indexing groove 88 in the delivery unit 62. An indexing notch 90 in the housing's front end 81 communicates with the indexing groove 88 as the unit 62 is pushed into place.

When the delivery unit 62 is indexed and secured in the main housing 16, the piston's foot ends in threaded cap 70 which engages the recess 71 in the drive piston 56, such that the biasing spring 66 is slightly compressed. Accordingly, when the quick disconnect mechanism 80 is depressed and the delivery unit 62 is released, the biasing spring 66 partially ejects the delivery unit 62 from the main housing 16.

Figure 2:
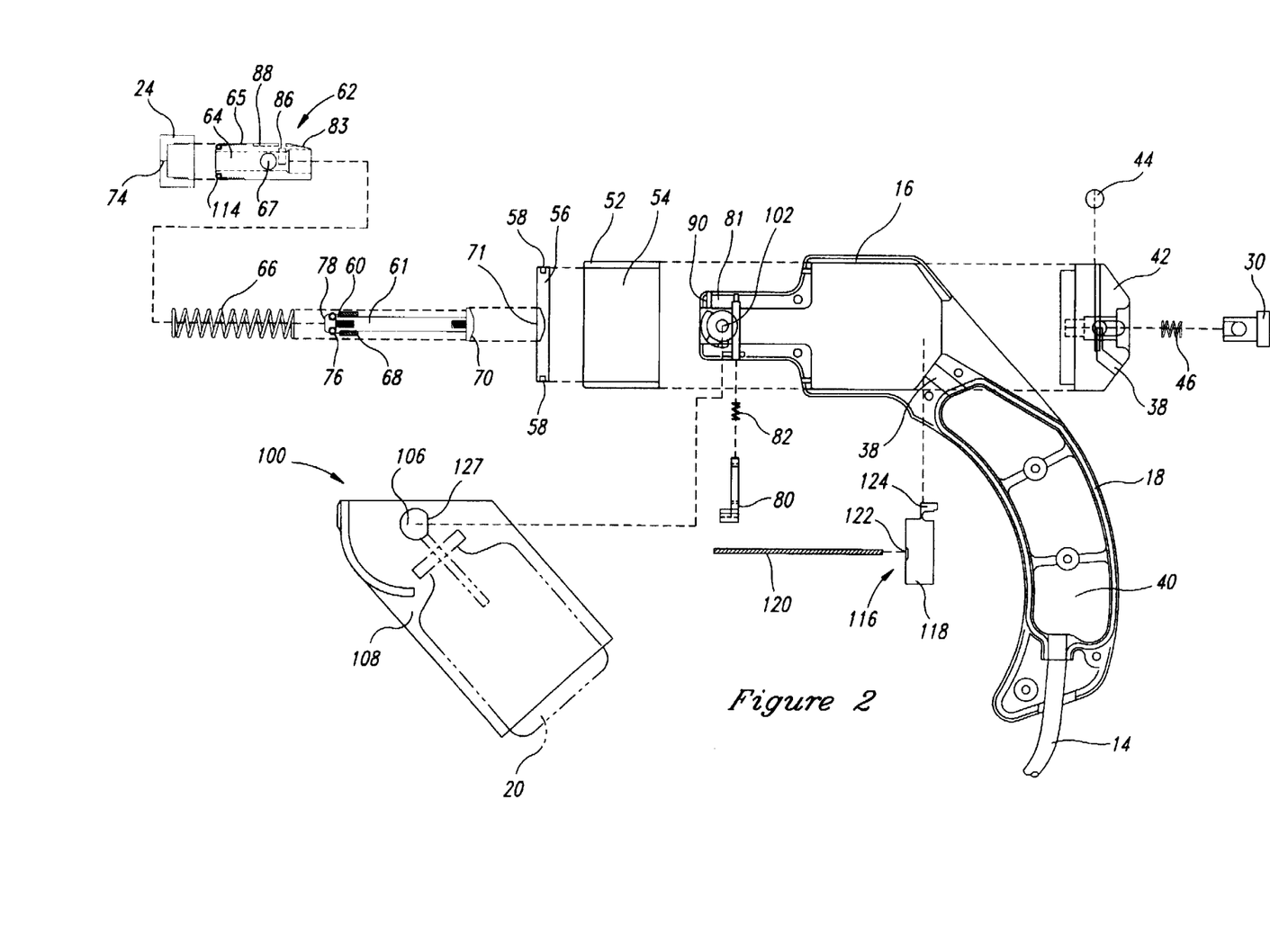
FIG. 2 is an exploded side view of the needleless injector.
Figure 4:
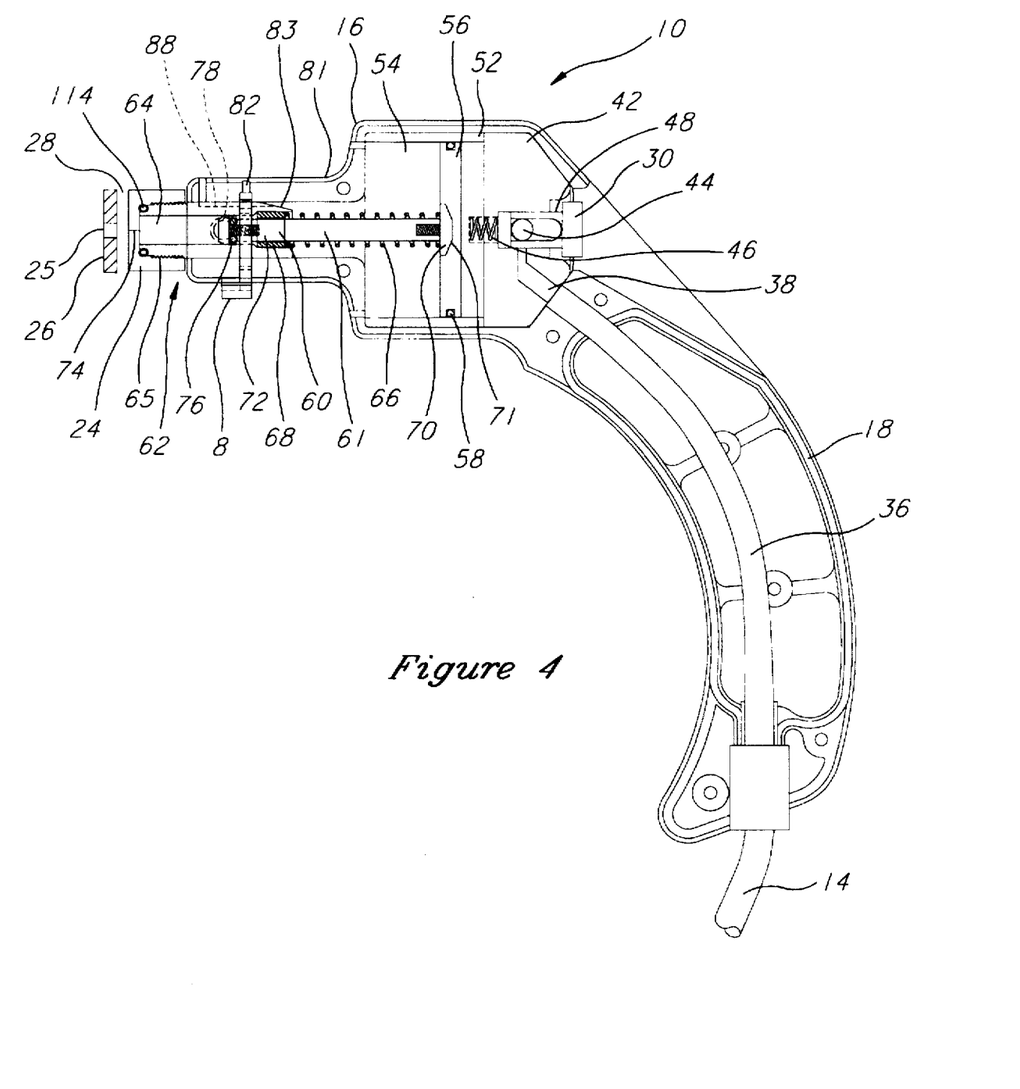
FIG. 4 is a side cross-section view of the needleless injector along line 4—4 in FIG. 3A.

In the preferred embodiment, the housing 16 and handle 18 are made of a durable and lightweight plastic, and the medicine delivery unit 62 is primarily made of stainless steel components. The entire steel delivery unit 62 may be quickly ejected from the needleless hypodermic injector assembly 10, dropped into a sterilizing bath, and a new, sterile delivery unit may be inserted within the needleless hypodermic injector assembly 10. This sequence can be accomplished in a matter of seconds, and the assembly is ready for safe injections with the same or a different medicine. Thus the invention makes possible a lightweight ergonomic design having a long useful life and providing economical, easily sterilizable use in rural clinics having few amenities.

Medicine enters the medicine chamber 64 through the unit's fill port 67 during a filling process. The fill port 67 is located very close to the piston head 78 when the piston 60 is in its retracted position 72. Accordingly, the fill port 67 is positioned so as to be closed at the beginning of the piston's discharge stroke. Such positioning of the fill port 67 alleviates the requirement of a check valve to prevent medicine from flowing out of the fill port 67 during the discharge stroke. In the preferred embodiment, the fill port 67 is a small orifice normally about 10 thousandths of an inch in diameter and about 10–20 thousandths of an inch long through which a medicine dose of approximately 0.5 ml is transferred into the medicine chamber.

The needleless hypodermic injector assembly 10 further includes a removable medicine chamber filling mechanism 100, which includes a medicine distributor 106 and a medicine vial holder 108, described in greater detail below, that engages the housing 16. A filling nozzle 104 on the filling mechanism 100 is received by the housing 16 through a passage 102 located in the housing's front end 81. The passage 102 coaxially aligns the nozzle 104 with the fill port 67 when delivery unit 62 has been properly installed. Accordingly, medicine may be transported into the medicine chamber 64 through the nozzle 104 and fill port 67 by using positive pressure to force the medicine into the medicine chamber 64. The delivery unit 62 indicates when the filling mechanism 100 has completely filled the medicine chamber 64 when medicine begins to dribble through the nozzle's orifice 74.

When the filling mechanism 100 and associated spacer 26 engage the housing 16, the filling mechanism 100 and spacer 26 may be pivoted from a "ready to fire" position 110, with the spacer 26 in front of the nozzle 24, to a raised "filling position" 112 (FIG. 6, discussed in detail below), with the spacer 26 moved away from the nozzle 24. Once in the filling position 112, the medicine distributor 106 is used to push medicine through the nozzle 104 and filling port 67 and into the medicine chamber 64. In the preferred embodiment, the spacer 26 is integral to the removable filling mechanism 100, and when pivoted into the "ready to fire" position 110, the resulting air gap has a range from about 1.5 mm to 4.0 mm. The preferred size is about 3.5 mm. It is to be recognized that the spacer 26 may be movably mounted to other structures of the needleless hypodermic injector assembly 10 and still achieve the goal of maintaining an air gap 28 between the nozzle 24 and the patient. The spacer 26 has a small opening 25 through which the highly focused stream of medicine passes. For the preferred gap distances given above, an opening of about 4 mm. is preferred. This combination of gap distance and size of opening 25 have been found highly efficient in reducing splash-back, contact and capillary contamination of medicine and blood from contaminating the nozzle as compared to prior devices (such as a recessed nozzle orifice) which permit bunching of a patient's skin and otherwise do not adequately shield the nozzle and orifice from contamination.

The needleless hypodermic injector assembly 10 may be prohibited from firing by a safety mechanism 116. The safety 116 includes a safety interlock 118 and a safety rod 120 within the housing 16. The safety interlock 118, which has a foot 124 and a notch 122, engages the firing button 30. One end of the safety rod 120 communicates with the notch 122, and the other end communicates with the medicine distributor 106. When the safety interlock 118 is pressed inward to the "safe" position 123 (FIG. 3A), the rod 120 rests within the notch 122. In this position, the safety rod 120 does not extend into the medicine distributor 106 and interfere with the rotation of distributor 106. A cam is provided in medicine distributor 106 by means of a slot 127 along an arc of distributor 106. When the safety interlock 118 is withdrawn to the "fire position" 125 (FIG. 3B), the safety rod 120 moves out of the notch 122 and extends into the slot 127, thereby interfering with the flat face of slot 127 (FIG. 3A) on the distributor 106. This interference prevents the filling mechanism 100 from being pivoted into the filling position 112. Thus, when refilling of the medicine chamber 64 is desired, the safety interlock 118 must be moved to the "safe" position 123.

The safety interlock's foot 124 is positioned within the housing 16, such that the foot 124 directly communicates with the activation valve 44. In addition, a fire button block 126 prevents the button 30 from being depressed when the safety interlock 118 is in the safe position 123. The safety interlock's motion into and out of the main housing 16 is limited by a pin 130 within slot 131 adjacent to the foot 124.

Figure 3A:
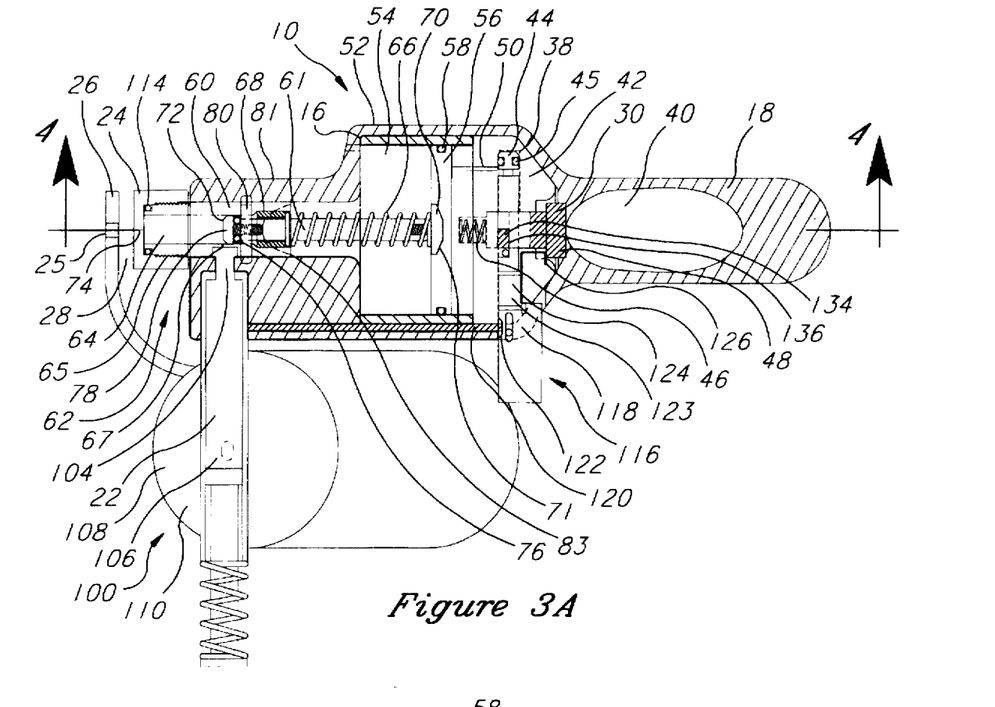
FIG. 3A is a plan view of the needleless injector with a schematic representation of an attached medicine chamber filling mechanism and spacer.
Figure 3B:
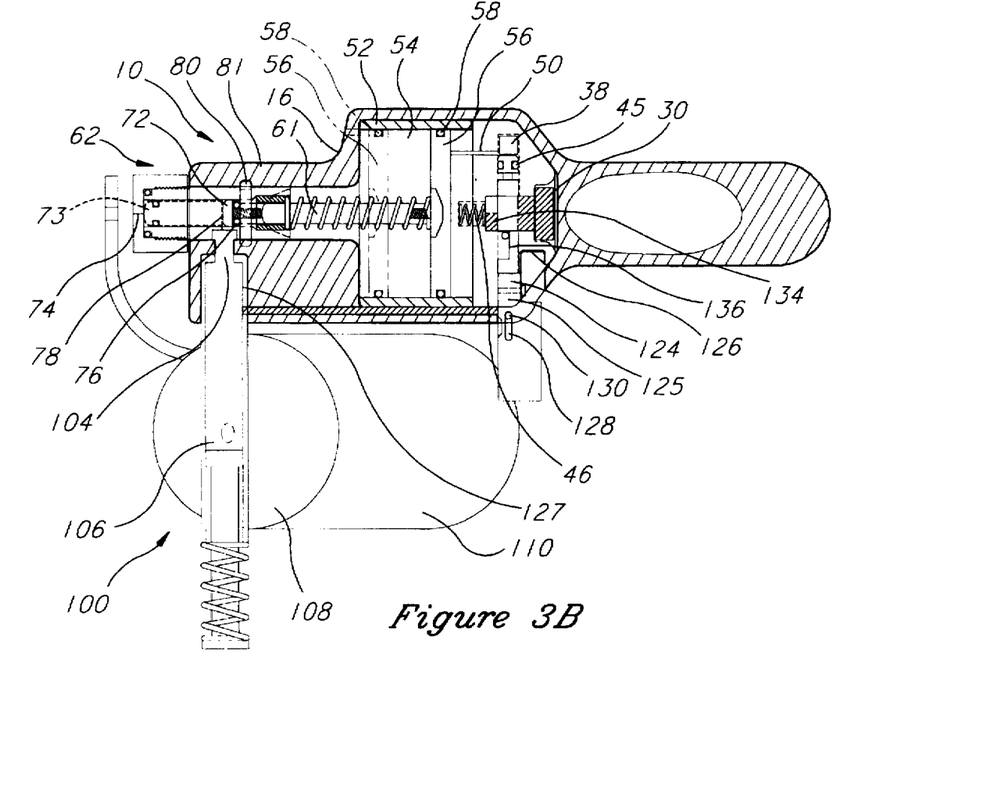
FIG. 3B is a partial plan view of the needleless injector with the fire button and activation valve in the fired position.

When the needleless hypodermic injector is ready to fire, as best seen in FIG. 3A, the activation valve 44 is closed, the low pressure air supply is blocked, and the air piston 56 and delivery piston 60 are at rest in the retracted position. A valve block 134 on the fire button 30 fits into a notch 136 in the activation valve 44. When the fire button 30 is pressed in, as best seen in FIG. 3B, the valve block 134 moves forwardly out of the notch 136, thereby allowing the activation valve 44 to slide from the closed position to an open position, whereat the pressurized air moves from passage 38 to port 50. The pressurized air within the passage 38 is sufficiently strong to instantaneously drive the activation valve 44 to the open position. Although an operator can depress the fire button 30 with different velocities or different forces, the velocity or extent of force used is independent of the speed in which said activating valve 44 will move to the open position. Once the valve block is no longer interfering with the activation valve 44, the valve will snap to the open position.

After the needleless hypodermic injector has been fired, the safety interlock 118 must be returned to the "safe" position 123 in order to refill the medicine chamber 64. As the safety interlock 118 moves into the housing 16, the foot 124 engages the activation valve 44 and drives the valve 44 back to the closed position. In addition, the fire button's spring 46 forces the valve block 134 back into the notch 136 so as to prevent the valve 44 from sliding back to the open position.

In another embodiment of the present invention, the safety interlock is interconnected with the filling mechanism 100 and the spacer 26, such that the safety interlock 118 may not be moved to the "fire position" until the spacer 26 has been moved to a particular predetermined orientation relative to the nozzle 24.

In the preferred embodiment of the needleless hypodermic injector assembly 10, the low pressure air from the pump 12 has a pressure in the range of about 50 to 250 pounds per square inch (gauge) (psig). Good performance is achieved when the starting pressure is in the range of about 80 psig to 140 psig. During an injection, the air pressure within the assembly 10 drops, and after the injection, the pressurized air in the assembly 10 is in the range of about 60 psig to 100 psig. When the source of low pressure air is provided by a foot pump, a preferred embodiment is to have an accumulator maintained at a base pressure of about 65–70 psig by a spring. A single stroke of an air pump raises this pressure to about 80 psig. After an injection, the pressure drops to the base pressure.

Upon firing the assembly, the low pressure air drives the pistons 56 and 60 forward, and the medicine within the medicine chamber 64 achieves a pressure in the range of about 2,500 psi to 4,500 psi as the fluid is forced through the nozzle's shaped orifice 74. It is preferred that the fluid stream have either a coherent cylindrical configuration or a cone shape with the apex at or just beyond the outer side of opening 25. One way of producing the desired fluid stream shape is to use a cylindrical orifice 74, optionally with the upstream edge created by a spherical counterbore. In a preferred embodiment orifice 74 has a diameter of about 6 thousandths of an inch and a length of about 15–18 thousandths of an inch. The resulting high pressure fluid stream has a diameter ranging from about 0.004 inch to 0.008 inch, which is smaller than most hypodermic needles. This high pressure within the medicine chamber 64 is generated by the low pressure air because of the relationship between the air piston's surface area and the discharge piston's surface area in the medicine chamber. The ratio between the surface areas utilized ranges from about 13:1 to 155:1. The preferred area ratio is about 64:1. It is to be noted that these ranges represent the design of the preferred embodiment, but the ranges are not to limit the scope of this patent.

In a second embodiment of the needleless hypodermic injector assembly 10, as best seen in FIG. 2, the low pressure air hose 14 enters an on-board air chamber 40 that, in turn, connects to the air passage 38. The chamber 40 holds enough pressurized air for the discharge assembly 10 to administer at least one injection. Thus, after the pump 12 pressurizes the air within the chamber 40, the hose 14 can be removed, and the delivery assembly 10 may be transported away from the air source 12 to give an injection. The mobility of this embodiment allows for substantial flexibility in using the assembly 10.

Figure 5:
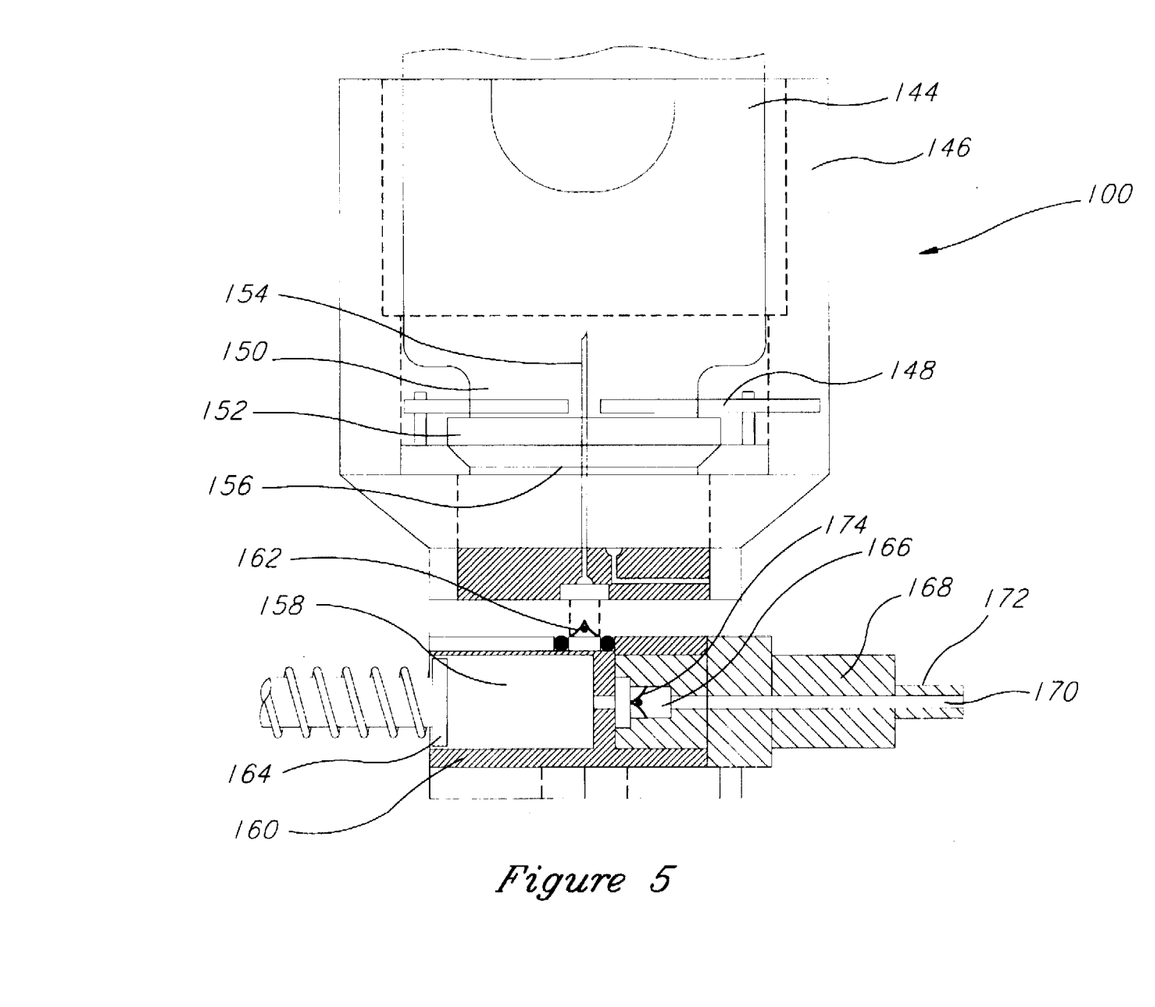
FIG. 5 is a side cross-section view of the removable medicine chamber filling, mechanism.

Referring now to FIGS. 3 and 5, the removable filling mechanism 100 includes a medicine vial holder 108 operatively connected to a medicine distributor 106. The medicine distributor 106 utilizes positive pressure to distribute medicine from a vial 144 into the first medicine chamber 64.

The vial holder 108 has a vial receiving unit 146 with a clamping mechanism 148 that clamps the vial 144 into the receiving unit 146. In the preferred embodiment, the clamp 148 comprises a scissor-type clamp that engages the vial 144 around the vial's necked portion 150 adjacent to the vial's cap 152. The scissor clamp 148 allows for different sized vials to be securely held within the receiving unit 146.

The vial holder 108 uses a medicine transport mechanism, such as a hollow needle 154, to pierce a membrane 156 on the vial 144 and gain access to the medicine therein. The medicine is drawn from the vial 144, through the hollow needle 154, through second filling port 162 and into a second medicine chamber 158 formed by a distributor housing 160. The medicine is prevented from flowing back into the vial 144 by a check valve 162 located between the second chamber 158 and the needle 154.

The medicine is drawn into the second chamber 158 by withdrawing a plunger 164 that is slidably mounted in the chamber 158 while check valve 174 prevents the entrance of air through distributor orifice 170 from delivery unit 62. After medicine has filled the chamber 158, the plunger 164 is used to generate positive pressure that drives the medicine through a channel 166 in the filler tube 168, and through the distributor orifice 170. During operation of the medicine delivery assembly 10, medicine is prevented from flowing back through the distributor orifice 170 toward the vial 144 by a check valve 174 located at the beginning of the channel 166. The filler tube 168 includes a filler nozzle 172 having a predetermined size allowing for efficient transfer of medicine from the filler nozzle 172 into the first medicine chamber 64 through the filler ports 102 and 67. In another embodiment, a button operated pump diaphragm is substituted for plunger 164. A first depression of the button fills the chamber 158 and subsequent depressions provide the positive pressure that drives the medicine into the medicine chamber 64 and refills the chamber 158.

Figure 6:
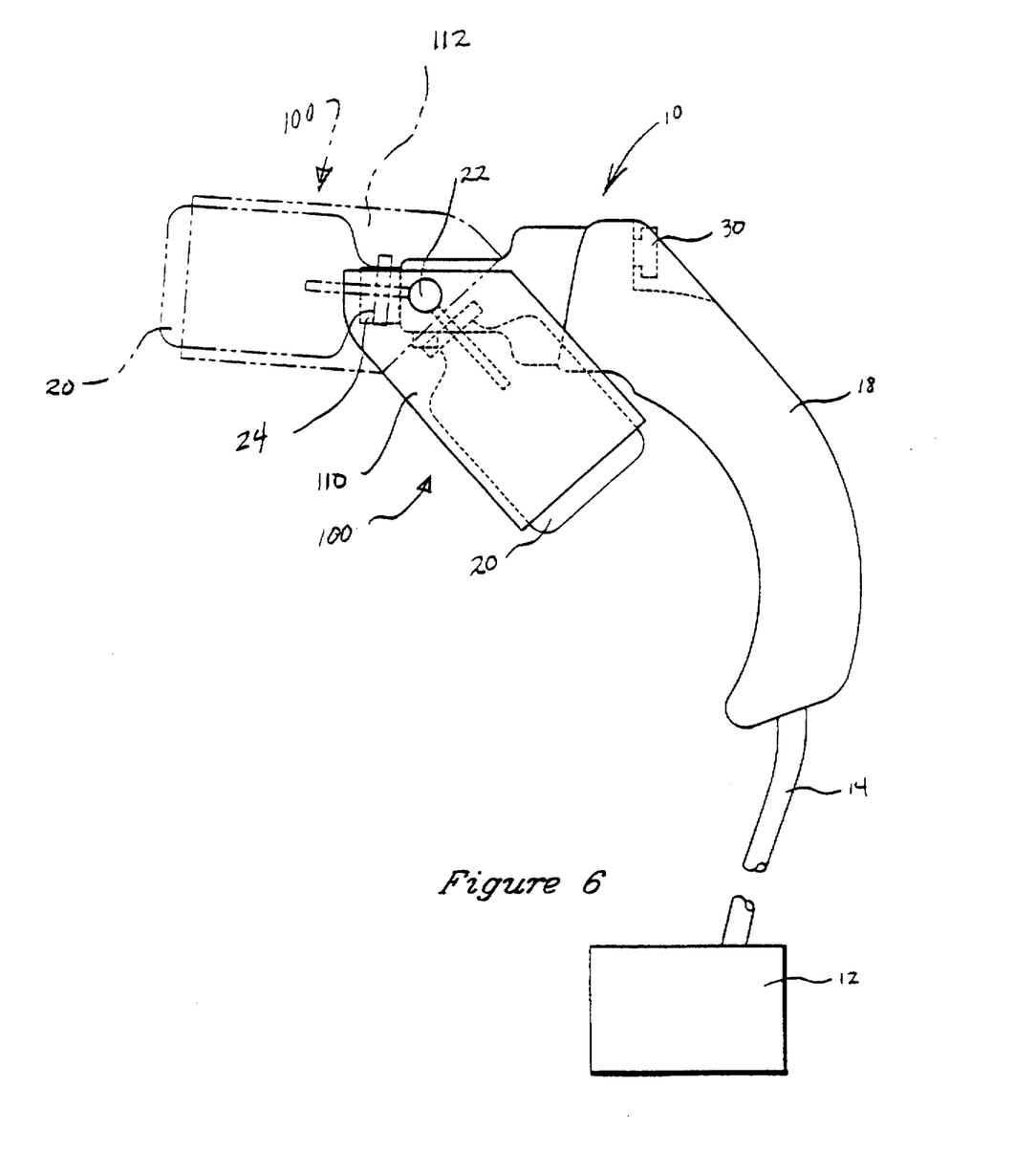
FIG. 6 is a schematic representation of the needleless injector with an attached medicine chamber filling mechanism shown in two operative positions.

As indicated above, a new dose of medicine must be loaded into the first medicine chamber 64 after each injection. Referring to FIG. 6, the medicine chamber filling mechanism 100 can pivot to the loading position 112 as the medicine delivery assembly 10 is oriented such that the vial 144 is coaxially aligned with the nozzle 24. When the assembly is pointed upward, the medicine in the vial 144 covers the needle 154. After a dose of medicine has been loaded into the first medicine chamber 64, and the filling mechanism 100 is pivoted back to the injecting position 110, the safety interlock 118 may be moved to the fire position 125, and the medicine delivery assembly is ready to deliver a dose of medicine upon depressing the fire button 30.

Obviously, numerous modifications and variations of the medicine delivery assembly disclosed herein will occur to those skilled in the art in view of this disclosure. Therefore, it is expressly to be understood that these modifications and variations, and the equivalents thereof, may be practiced while remaining within the spirit and scope of the invention as defined in the following claims.

We claim:

1. A needleless hypodermic injector comprising:

a main housing containing an air chamber for receiving air at a pressure between about 50 to 250 pounds per square inch gauge, a driving piston slidably mounted in said chamber, injection activating means to admit pressurized air to said chamber to activate the driving piston, and means for connecting said chamber to a source of air at a pressure between about 50 to 250 pounds per square inch gauge; and a medicine delivery unit comprising means to detachably mount said delivery unit to said main housing, a medicine chamber with a side wall and a medicine fill port in said side wall of said medicine chamber, said fill port adapted to be connected to a source supplying medicament to said fill port under positive pressure, a discharge nozzle valvelessly connecting one end of said medicine chamber to an ejection orifice with a substantially total absence of dead space between said chamber and said ejection orifice, a discharge piston in said medicine chamber, said discharge piston detachably engaging said driving piston when said delivery unit is mounted in said main housing and is detached from said driving piston when said delivery unit is detached from said main housing, and biasing means urging said discharge piston to an end of said medicine chamber opposite from said discharge nozzle.

2. The needleless hypodermic injector of claim 1 further comprising a removable medicine filling mechanism detachably engaging said main housing, said filling mechanism comprising a vial holder, a medicine distributor and liquid transfer means to transfer liquid from a vial to said medicine chamber.

3. The needleless hypodermic injector of claim 2 wherein said medicine filling mechanism is movable to an activation position, and further comprising a safety interlock coupled to said injection activating means to prevent inadvertent activation thereof when said medicine filling mechanism is not in said activation position.

4. The needleless hypodermic injector of claim 3 having a spacer with an opening therein to allow a medicament stream expelled from said nozzle by said discharge piston to pass therethrough, said spacer being positioned adjacent to said nozzle thereby forming an air gap between said nozzle and said spacer and consequently spacing said nozzle from contact with the surface to be injected, and further comprising connecting means to connect said spacer to said safety interlock.

5. The needleless hypodermic injector of claim 2 wherein said removable medicine filling mechanism is operatively moved between two distinct positions relative to said main housing, one position for the filling of medicine into said medicine chamber, and the other position for the activation of said injection activating means.

6. The needleless hypodermic injector of claim 2 wherein said medicine distributor comprises a housing forming a second medicine chamber adapted to contain the liquid therein and having an orifice at one end operatively engaging said fill port when said filling mechanism engages said main housing, said liquid transfer means operatively connecting said vial holder and said second medicine chamber and means to apply positive pressure to the liquid in said second medicine chamber to force the liquid from said second medicine chamber through said orifice in said second medicine chamber, through said fill port and into said medicine chamber in said delivery unit.

7. The needleless hypodermic injector of claim 6 wherein said vial holder comprises a vial receiving unit and a clamping mechanism to clamp the vial in said receiving unit; and said means to apply positive pressure to said second medicine chamber comprises plunger means slidably carried in said second medicine chamber and means to activate said plunger to move through said second medicine chamber applying positive pressure to transfer the liquid from said second medicine chamber through said orifice in said second medicine chamber and said fill port and into said medicine chamber in said delivery unit.

8. The needleless hypodermic injector of claim 7 wherein said plunger means when released generates negative pressure transferring the liquid from the vial, through said liquid transfer means and into said second medicine chamber.

9. The needleless hypodermic injector of claim 2 having a spacer with an opening therein to allow a medicament stream expelled from said nozzle by said discharge piston to pass therethrough, said spacer being positioned adjacent to said nozzle thereby forming an air gap between said nozzle and said spacer and consequently spacing said nozzle from contact with the surface to be injected, wherein said spacer is movably carried by said filling mechanism and said air gap has a length from about 1.5 mm. to about 4.0 mm.

10. The needleless hypodermic injector of claim 1 wherein said activating means comprises firing means, restraining means, and an activation valve, said activation valve snapping from closed to open position under air pressure alone when said restraining means releases said activation valve.

11. The needleless hypodermic injector of claim 1 having a planar spacer positioned to provide an air gap of about 1.5 lto 4 mm from said discharge nozzle, said spacer having a small opening therein to allow a medicine stream of medicine expelled from said discharge nozzle to pass therethrough while preventing said discharge nozzle from contacting any bunched skin of the patient being injected.

12. The needleless hypodermic injector of claim 11 wherein said discharge nozzle has a shaped orifice to create a focused medicine stream as the medicine is forced out of said first medicine chamber through said nozzle and through said opening in said spacer.

13. The needleless hypodermic injector of claim 12 having said spacer movably carried by a medicine filling mechanism engaging said main housing such that when said filling mechanism is moved between a filling position and an injection activation position, said spacer is respectively self positioned away from said nozzle during filling and is self positioned adjacent to said nozzle during injection, thereby forming said air gap between said nozzle and said spacer.

* * * * *